United States Patent [19]

Fox

[11] 4,246,243
[45] Jan. 20, 1981

[54] USE OF STEEL PLANT WASTE DUSTS FOR SCAVENGING HYDROGEN SULFIDE

[76] Inventor: Irwin Fox, 37 Meadowbrook Country Club Estates, Ballwin, Mo.

[21] Appl. No.: 963,797

[22] Filed: Nov. 27, 1978

Related U.S. Application Data

[63] Continuation-in-part of Ser. No. 941,314, Sep. 11, 1978, abandoned, Ser. No. 939,441, Sep. 5, 1978, and Ser. No. 754,543, Dec. 27, 1976, abandoned, which is a continuation-in-part of Ser. No. 666,760, Mar. 16, 1976, abandoned, and Ser. No. 666,193, Mar. 12, 1976, Pat. No. 4,008,775, said Ser. No. 666,760, and Ser. No. 666,193, each is a continuation-in-part of Ser. No. 374,555, Jun. 28, 1973, abandoned, said Ser. No. 939,441, is a continuation-in-part of Ser. No. 666,760, , abandoned.

[51] Int. Cl.$^3$ .................... B01D 53/34; C09K 7/04
[52] U.S. Cl. .................... 423/225; 423/231; 423/562; 423/632; 423/573 G; 252/8.5 B; 252/8.55 B; 175/64; 75/25
[58] Field of Search .............. 423/230, 231, 225, 562, 423/573 G, 632, 633; 175/64, 66; 75/25; 252/8.5 E, 8.55 B, 8.55 E

[56] References Cited

U.S. PATENT DOCUMENTS

| | | | |
|---|---|---|---|
| 1,160,375 | 11/1915 | Burkheisen | 423/225 |
| 1,734,307 | 11/1929 | Sperr, Jr. | 423/225 |
| 1,849,428 | 3/1932 | Laux | 423/632 |
| 2,122,236 | 6/1938 | Nichols et al. | 252/8.5 B |
| 3,301,323 | 1/1967 | Parsons | 175/64 |
| 3,887,474 | 6/1975 | Senfe et al. | 423/633 X |
| 4,008,775 | 2/1977 | Fox | 175/64 |
| 4,025,604 | 5/1977 | Morlguchi et al. | 423/239 A |

FOREIGN PATENT DOCUMENTS 495690  9/1953  Canada .................................... 423/632

OTHER PUBLICATIONS

Milbourne, "The Removal of Hydrogen Sulfide From Gas By Means of Iron Oxide With Special Reference to Humidity Conditions", John Hopkins University, 1930, pp. 9 & 10.

Primary Examiner—Earl C. Thomas
Attorney, Agent, or Firm—Jerome A. Gross

[57] ABSTRACT

Iron rich dusts created during steelmaking, as in the basic oxygen and open hearth processes, are useful for scavenging hydrogen sulfide. For example, basic oxygen furnace dusts, which are in more abundant supply, are found to consist of fine, nearly spherical particles of iron oxide whose crystalline composition comprises $Fe_3O_4$ (major portion) and $Fe_2O_3$ (minor portion) as seen by X-ray diffraction. Their great surface area makes them highly reactive to hydrogen sulfide gas. Their reaction yields unexpected products, namely, free sulfur and iron hydroxides. According to the present invention such iron rich dusts are used in water slurries through which sour hydrocarbon gas is bubbled, and in water based drilling muds to scavenge hydrogen sulfide encountered in well drilling.

4 Claims, No Drawings

USE OF STEEL PLANT WASTE DUSTS FOR SCAVENGING HYDROGEN SULFIDE

CROSS REFERENCE TO RELATED APPLICATIONS

This application is a continuation-in-part of both Ser. No. 941,314, filed Sept. 11, 1978, entitled SLURRY METHOD AND APPARATUS FOR SWEETENING HYDROCARBON GAS, now abandoned; and of Ser. No. 754,453, filed Dec. 27, 1976, entitled STEEL PLANT WASTE DUSTS FOR SCAVENGING HYDROGEN SULFIDE, now abandoned; which Ser. No. 754,453 is a continuation-in-part of the following applications:

Ser. No. 666,193, filed Mar. 12, 1976, entitled METHOD OF USING A POROUS $Fe_3O_4$ DRILLING MUD ADDITIVE, now U.S. Pat. No. 4,008,775, issued Feb. 22, 1977; and Ser. No. 666,760, filed Mar. 16, 1976, entitled SLURRY METHOD AND APPARATUS FOR SWEETENING HYDROBARBON GAS, now abandoned; both of which applications are continuations-in-part of Ser. No. 374,555, filed June 28, 1973, entitled POROUS $Fe_3O_4$ DRILLING MUD ADDITIVE, now abandoned;

This application is also a continuation-in-part of Ser. No. 939,441, filed Sept. 5, 1978, entitled SLURRY METHOD FOR SWEETENING HYDROCARBON GAS, co-pending but to be abandoned, which is a continuation-in-part of said application Ser. No. 666,760.

BACKGROUND OF THE INVENTION

Iron rich dusts derived from various steelmaking processes have been generally thought to be the common iron oxide $Fe_2O_3$. These ducts are wastes, with limited use for such minor purposes as a hardener for cement. There have been attempts at reclamation for recycling to steel furnaces. U.S. Pat. No. 3,895,088, issued July 15, 1975, to Michigan Technological University identifies and describes these ducts.

It is well known that hydrogen sulfide gas may be extracted from hydrocarbon gas by reacting with iron compounds; for example, sour fuel gas is pumped through trays of wood chips impregnated with $Fe_2O_3$. Likewise, hydrocarbon gas may be bubbled through an aqueous solution of iron hydroxides, with the following reaction:

$$2Fe(OH)_3 + 3H_2S \rightleftharpoons Fe_2S_3 + 6H_2O$$

The reaction product $Fe_2S_3$ is unstable; regeneration is to be expected.

In my earlier co-pending applications previously referred to, I disclosed a quite different type of iron oxide particle characterized by exceptional porosity and created by the partial oxidation of iron to $Fe_3O_4$. This may be used for sweetening gas by making a water slurry of such particles and bubbling the gas through the slurry, with stable products of reaction. In my earlier application, now U.S. Pat. No. 4,008,775, I disclosed that such porous particles are advantageously used as an additive to water based muds in the drilling of wells.

FIELD OF THE INVENTION

The present invention relates to scavenging hydrogen sulfide gas, as may be present in hydrocarbon fuel gases or encountered in well drilling. A new use is found for the iron oxide dusts formed in steelmaking.

SUMMARY OF THE INVENTION

The present invention provides a new use for the fine particulate iron rich dusts of steelmaking. Basic oxygen and open hearth dust particles are exceptionally small sized; though lacking the porosity of the larger particles described in my said co-pending applications, they possess tremendous total surface area for reaction. When suspended in an aqueous fluid, the tiny particles react so rapidly with hydrogen sulfide gas as to be an effective scavenger. Surprisingly they yield unexpected and non-polluting products of reaction, both free sulfur and iron hydroxides.

Two principal uses are here described. In one, the aqueous fluid is a heavy slurry of the particles in water, through which hydrocarbon gas contaminated by hydrogen sulfide is bubbled. In the second use, the fluid in which they are suspended is a water based well drilling mud; hydrogen sulfide, gas escaping from the formation wall as a well is drilled, is entrained in the mud and reacted by the suspended particles.

The present particles vary somewhat in color, but ordinarily present a brownish appearance characteristic of the common iron oxide $Fe_2O_3$. This compound, on reaction with hydrogen sulfide, would yield FeS, which is unstable. Instead, free sulfur and iron hydroxides are found to be the reaction products. These permit safe disposal, without danger to the environment.

DESCRIPTION OF THE PREFERRED EMBODIMENT

In the methods of the present invention, advantage is taken of the unique physical properties of the iron-rich dusts from steelmaking and the fact that the products of their reaction with hydrogen sulfide are unexpectedly stable.

As to the physical and chemical properties of these dusts, relatively little appears to have been published. The best source known to applicant is U.S. Pat. No. 3,895,088, issued to Michigan Technological University. This patent describes these dusts as waste products; dealers in wastes have considered them to be in pure iron oxide $Fe_2O_3$.

The patent to Michigan Technological University, furnishes chemical analyses of these dusts, showing the quantity of iron present as an element, rather than in compounds. Iron generally accounts for somewhat more than 60% by weight of the dusts from the various steelmaking processes, excluding water present from the process of collection. From a chemical standpoint, the dusts which appear to be the most similar are those from the basic oxygen process and the open hearth process. The basic oxygen furnace dust is referred to as BOF.

The physical properties of the BOF dust and open hearth dust are quite similar. The Michigan Technological University patent states, and electronmicroscopy confirms, that BOF particles are usually spherical in shape, with about 80% being smaller than 0.5 microns. Open hearth dust is chemically and physically quite similar, but contains less slag and overburned lime. This similarity results from similar conditions in their formation. The particles are formed upon rapid solidification of iron droplets or vapor upon contact with the cover surfaces of the furnace flues. Such rapid solidification and the presence of the impurities described above inhibit crystallite formation leaving substantial amorphorous iron oxide. Substantially all particles should pass through a 325 mesh screen, U.S. Standard, and the majority through a 500 mesh screen. BOF dusts typically contain some slag, overburned lime and graphite and, depending upon the type of scrap used as part of a charge to the process, may include some zinc, lead and other metallic elements.

According to the Michigan Technological University patent, chemical analyses of these dusts are as follows:

|  | BOF Dust | Open Hearth Dust |
|---|---|---|
| Fe | 61.47 | 65.42 |
| CuO | 5.15 | 0.52 |
| MgO | 1.30 | 0.13 |
| SiO$_2$ | 2.04 | 0.42 |
| Al$_2$O$_3$ | 0.09 | 0.05 |
| Zn | 1.06 | 0.35 |
| Pb | 0.17 | 0.70 |
| S | 0.10 | 0.05 |
| P | 0.12 | 0.34 |
| Na | 0.18 | 0.02 |
| K | 0.37 | 0.34 |
| C | 0.23 | 0.22 |

Test Data

Surface Area:

Tests of surface area, carried on by the Sor-Bet and Absorptomat methods, reveal that the basic oxygen furnace dusts have a surface area of about 7.1 square meters per gram. Samples will vary; dust with an effective surface area of 4.0 square meters per gram or greater is deemed to be suitable for practicing the present methods.

Reaction efficiency:

Tests were made by adding pure hydrogen sulfide to the reactor vessel while allowing all excess to flow through a drager detector to determine the "breakthrough" point. Flow was then diverted to a trap in order to measure the amount not being reacted. The maximum flow rate without a "breakthrough" was determined. The sulfides in the reactor and the trap were determined using the API Gas Train Method. The amount of hydrogen sulfide added was determined by weighing the lecture bomb containing the hydrogen sulfide before and after additions. Twenty-eight grams of BOF dust were used in 500 ml. of water. It was observed that 14.7 grams per hour of hydrogen sulfide were removed. The reaction efficiency was then calculated by dividing the sum of the sulfides in the reactor plus the trap by the weight percent of hydrogen sulfide added. The calculated efficiency of removal was 96% of the hydrogen sulfide added during the test.

Fe$^{++}$, Fe$^{+++}$ Titration:

Further understanding of the BOF material was gained by contrasting X-ray diffraction analysis with an ion titration assay . X-ray diffraction analysis shows that although a small amount of crystalline Fe$_2$O$_3$ is present, the major portion of crystalline iron oxide is Fe$_3$O$_4$. The titration data summarized hereinafter indicates that a substantial amount of the total Fe$^{+++}$ iron is non-crystalline. This Fe$^{+++}$ iron appears to be present in an amount intermediate to that for pure standards of Fe$_3$O$_4$ and Fe$_2$O$_3$, and in an amorphous state covalently bonded with oxygen. Such Fe$^{+++}$ iron not incorporated into any crystalline lattice, may enter more quickly into reaction with H$_2$S.

Ion titrations utilizing the method of Kolthoff, I. M. and E. B. Sandell, *Quantitative Inorganic Analysis,* 3d ed. (1952), were carried out on BOF dust. The results, comparing the Fe$^{++}$ and Fe$^{+++}$ content of BOF dust to an Fe$_3$O$_4$ standard (Bisberg, Sweden) are as follows:

|  | Fe$_3$O$_4$ Pure Standard | Fe$_2$O$_3$ Standard | BOF |
|---|---|---|---|
| Total iron | 72.3 | 70.0 | 61.8 |
| % Fe$^{++}$ | 27.6 | 2.8 | 3.6 |
| % Fe$^{+++}$ | 47.7 | 67.2 | 58.2 |

Products of reaction:

The reaction products of the foregoing test were analyzed and found to be free sulfur and iron hydroxides. This contrasts with the expected product of reaction with Fe$_2$O$_3$, which would be principally FeS. While no explanation is offered for the unexpected result, it is noted that in reacting iron oxides with hydrogen sulfide, a number of competing reactions occur simultaneously; possibly metallic impurities found in the waste dust may act catalytically to favor what otherwise might be a mere minor reaction.

Methods of Use

Use for sweetening fuel gas:

Using the apparatus described in my co-pending applications Ser. No. 939,441 whose disclosure is hereby incorporated by reference, water may be added to the present waste dust particles (in particular the BOF or open hearth process particles) to create a slurry whose weight is in the range of 10 to 20 pounds per barrel. The slurry is delivered into the lower portion of a pressure vessel having a head space, preferably with a mist eliminator and upper outlet. The inlet of the vessel is in the lower portion of the slurry, being connected to a source of sour gas.

The sour gas is admitted into the lower portion of the slurry through a pressure reducing valve, at a pressure sufficient to overcome the hydrostatic head of the slurry. Bubbling the pressurized gas through the slurry circulates and agitates it sufficiently to maintain the particles suspended; and the agitated circulation may be augmented by conventional mixing procedures.

As the gas passes through the slurry, the hydrogen sulfide in it reacts with the suspended particles, while the fuel gas passes up through the upper surface of the slurry, through the mist eliminator and to an outlet conduit.

The dust particles, spent by their reaction with the hydrogen sulfide gas, yield non-polluting reaction products consisting of free sulfur and iron hydroxides. The spent material is removed with the water and may be safely disposed of without danger to the environment.

Use in well drilling:

The procedures to be used may be as disclosed in my co-pending application Ser. No. 666,193, METHOD OF USING A POROUS Fe$_3$O$_4$ DRILLING MUD ADDITIVE, now U.S. Pat. No. 4,008,775, which is hereby incorporated by reference. A quantity of the fine iron rich dust particles, in particular the BOF or open hearth process particles, are added to drilling mud. The quantity is chosen to be sufficient to overcome emanations of hydrogen sulfide from the formation wal of the well being drilled, and may vary in the range of 2 to 20 pounds per barrel of mud. The fine powdery particles do not clump on being mixed into the water based mud but are suspended fairly evenly through it. On pumping the mud during drilling, as the mud rises from the drill bit up the formation wall the hydrogen sulfide will first be entrained in the mud and while entrained, reacted by the dust particles, to form ferrous hydroxide FeO(OH) and free sulfur. These may be safely removed and disposed of. The reaction with the hydrogen sulfide escaping from the formation wall may be expected to be complete; that is, the iron rich dusts will react with the hydrogen sulfide preferentially to its reaction with other iron present. Thus, it avoids corrosion and hydrogen embrittlement of the drill pipes, while it protects against contamination of the mud.

SUMMARY

The present invention thus provides new use for the waste dust particles derived from the fumes of steelmaking. They present a tremendously large surface area to react hydrogen sulfide so quickly as in effect to scavenge it. The products of reaction are unexpected; they do not regenerate. The spherical shape of the particles, (verified by electronmicroscopy as to BOF dusts) permits the fine powder particles to be used in water based drilling mud; they do not appear to adversely affect the rheological properties of the mud.

The open hearth dusts are so close in their physical and chemical properties to the BOF dusts that similar results are to be achieved. Likewise, other steelmaking dusts whose particles are of similar size and comprising roughly 60% iron will have similar effective properties.

I claim:

1. The process of scavenging hydrogen sulfide from drilling mud comprising the following steps:
   a. adding to water-based drilling mud the basic oxygen furnace particles from steelmaking, said particles having an iron oxide content of substantially 85% and being of somewhat spherical shape, the greater portion of which being smaller than 0.5 1 microns, said particles having a surface area of at least 4 square meters per gram as determined by the Absorptomat Method, in a quantity sufficient to react such hydrogen sulfide as may be encountered,
   b. circulating the drilling mud down the interior of the drill pipe, through the drill bit and up the annular space between the drill pipe and the formation wall to the surface,
   c. entraining in the circulating drilling mud such hydrogen sulfide as may be encountered, and
   d. reacting the entrained hydrogen sulfide with the said basic oxygen furnace dust particles under the pressure there present to form free sulfur and iron hydroxides.

2. The process of scavenging hydrogen sulfide from hydrocarbon gas comprising the following steps:
   a. adding to water basic oxygen furnace dust particles from steelmaking, said particles being of somewhat spherical shape, the greater portion of which being smaller than 0.5 microns, said particles having a surface of at least 4 square meters per gram as determined by the Absorptomat Method, to create a slurry whose weight is in the range of 10-20 lbs. per gallon,
   b. bubbling such hydrocarbon gas through said slurry, thereby causing contact between said particles and such gas,
   c. reacting such unwanted hydrogen sulfide from such hydrocarbon gas with said basic oxygen furnace dust particles to form free sulfur and iron hydroxides.

3. The process of scavenging unwanted hydrogen sulfide contained in hydrocarbon gas or drilling mud comprising the following steps:
   a. providing a water-based suspension of basic oxygen furnace dust particles from steelmaking, said particles having an iron oxide content of substantially 85% and being of somewhat spherical shape, the greater portion of which being smaller than 0.5 microns, said particles having a surface area of at least 4 square meters per gram as determined by the Absorptomat Method, in a quantity sufficient to react such hydrogen sulfide as may be encountered in such hydrocarbon gases or drilling mud,
   b. circulating said water-based suspension and causing said particles suspended therein to contact such hydrocarbon gases or drilling mud, and
   c. reacting the said hydrogen sulfide with said suspended basic oxygen furnace dust particles to form free sulfur and iron hydroxides.

4. The process of scavenging unwanted hydrogen sulfide contained in drilling mud comprising the following steps:
   a. providing a water-based suspension of those steelmaking waste dust particles selected from the group consisting of basic oxygen furnace dust and open hearth dust and formed by rapid solidification of iron in furnace flues, said steelmaking dust particles comprising $Fe^{+++}$ in an amount intermediate to that for pure standards of $Fe_3O_4$ and $Fe_2O_3$ and covalently bonded to oxygen in an amorphous state, together with crystalline iron oxide, said particles having a surface area of at least 4 square meters per gram as determined by the Absorptomat Method, in a quantity sufficient to react hydrogen sulfide as may be encountered in such hydrocarbon gases or drilling mud,
   b. circulating said water-based suspension and causing said particles suspended therein to contact such hydrocarbon gases or drilling mud, and
   c. reacting the said hydrogen sulfide with steelmaking waste dust particles to form free sulfur and iron hydroxide.

* * * * *

UNITED STATES PATENT AND TRADEMARK OFFICE
CERTIFICATE OF CORRECTION

PATENT NO. : 4,246,243
DATED : January 20, 1981
INVENTOR(S) : Irwin Fox

It is certified that error appears in the above-identified patent and that said Letters Patent are hereby corrected as shown below:

```
In column 1, line 37, delete "ducts" and insert ---dusts---.
In column 1, line 42, delete "ducts" and insert ---dusts---.
In column 4, line 68, delete "wal" and insert ---wall---.
In column 5, line 41, delete "l" at the end of the line.
```

Signed and Sealed this

Fourteenth Day of April 1981

[SEAL]

Attest:

RENE D. TEGTMEYER

Attesting Officer   Acting Commissioner of Patents and Trademarks